(12) United States Patent
Huang

(10) Patent No.: US 7,956,510 B2
(45) Date of Patent: Jun. 7, 2011

(54) MODULATION IN MICROMACHINED ULTRASONIC TRANSDUCERS

(75) Inventor: Yongli Huang, San Jose, CA (US)

(73) Assignee: Kolo Technologies, Inc., San Jose, CA (US)

( * ) Notice: Subject to any disclaimer, the term of this patent is extended or adjusted under 35 U.S.C. 154(b) by 145 days.

(21) Appl. No.: 12/296,099

(22) PCT Filed: Apr. 3, 2007

(86) PCT No.: PCT/US2007/065888
§ 371 (c)(1),
(2), (4) Date: Oct. 3, 2008

(87) PCT Pub. No.: WO2007/115283
PCT Pub. Date: Oct. 11, 2007

(65) Prior Publication Data
US 2009/0048522 A1    Feb. 19, 2009

Related U.S. Application Data

(60) Provisional application No. 60/744,242, filed on Apr. 4, 2006.

(51) Int. Cl.
*H02N 1/00* (2006.01)
(52) U.S. Cl. .................................................. 310/309

(58) Field of Classification Search .................. 310/309; 600/437, 459
See application file for complete search history.

(56) References Cited

U.S. PATENT DOCUMENTS

| | | |
|---|---|---|
| 6,945,115 B1 | 9/2005 | Wang |
| 2002/0048220 A1 | 4/2002 | Khuri-Yakub et al. |
| 2003/0039173 A1 | 2/2003 | Yurchenko et al. |
| 2003/0149363 A1 | 8/2003 | Dreschel et al. |
| 2004/0267134 A1 | 12/2004 | Hossack et al. |
| 2005/0075572 A1 | 4/2005 | Mills et al. |
| 2005/0101867 A1 | 5/2005 | Johnson et al. |
| 2005/0146240 A1* | 7/2005 | Smith et al. ............ 310/309 |
| 2006/0173342 A1 | 8/2006 | Panda et al. |
| 2006/0273805 A1 | 12/2006 | Peng et al. |
| 2007/0083119 A1 | 4/2007 | Adachi et al. |
| 2007/0287918 A1 | 12/2007 | Huang |
| 2009/0048522 A1 | 2/2009 | Huang |

* cited by examiner

*Primary Examiner* — Mark Budd
(74) *Attorney, Agent, or Firm* — Lee & Hayes, PLLC

(57) ABSTRACT

A capacitive micromachined ultrasonic transducer (cMUT) system uses a modulation technique to increase cMUT sensitivity. An AC carrier signal is applied to the cMUT through a modulation signal port to modulate the signal. The higher frequency of the AC carrier signal carries the real signal to a high frequency range to increase the output current signal level. The real signal is later recovered by demodulation. The technique is applicable in both the reception mode and the transmission mode.

25 Claims, 11 Drawing Sheets

US 7,956,510 B2

MODULATION IN MICROMACHINED ULTRASONIC TRANSDUCERS

PRIORITY

This application claims priority from U.S. Provisional Application Ser. No. 60/744,242, filed Apr. 4, 2006.

This application further incorporates herein by reference in entirety the following: U.S. patent application Ser. No. 11/695,919, entitled "SIGNAL CONTROL IN MICROMACHINED ULTRASONIC TRANSDUCER", filed on Apr. 3, 2007, by the common applicant.

BACKGROUND

The present invention relates capacitive micromachined ultrasonic transducers (cMUT), particularly to methods for operating cMUT.

Capacitive micromachined ultrasonic transducers (cMUTs) are electrostatic actuator/transducers, which are widely used in various applications. Ultrasonic transducers can operate in a variety of media including liquids, solids and gas. These transducers are commonly used for medical imaging for diagnostics and therapy, biochemical imaging, non-destructive evaluation of materials, sonar, communication, proximity sensors, gas flow measurements, in-situ process monitoring, acoustic microscopy, underwater sensing and imaging, and many others. In addition to discrete ultrasound transducers, ultrasound transducer arrays containing multiple transducers have been also developed. For example, two-dimensional arrays of ultrasound transducers are developed for imaging applications.

Compared to the widely used piezoelectric (PZT) ultrasound transducer, the MUT has advantages in device fabrication method, bandwidth and operation temperature. For example, making arrays of conventional PZT transducers involves dicing and connecting individual piezoelectric elements. This process is fraught with difficulties and high expenses, not to mention the large input impedance mismatch problem presented by such elements to transmit/receiving electronics. In comparison, the micromachining techniques used in fabricating MUTs are much more capable in making such arrays. In terms of performance, the MUT demonstrates a dynamic performance comparable to that of PZT transducers. For these reasons, the MUT is becoming an attractive alternative to the piezoelectric (PZT) ultrasound transducers.

The basic structure of a cMUT is a parallel plate capacitor with a rigid bottom electrode and a top electrode residing on or within a flexible membrane, which is used to transmit (TX) or detect (RX) an acoustic wave in an adjacent medium. A DC bias voltage is applied between the electrodes to deflect the membrane to an optimum position for cMUT operation, usually with the goal of maximizing sensitivity and bandwidth. During transmission an AC signal is applied to the transducer. The alternating electrostatic force between the top electrode and the bottom electrode actuates the membrane in order to deliver acoustic energy into the medium surrounding the cMUT. During reception the impinging acoustic wave vibrates the membrane, thus altering the capacitance between the two electrodes. An electronic circuit detects this capacitance change.

Two representative types of cMUT structures are conventional flexible membrane cMUT and the newer embedded-spring cMUT (ESCMUT). FIG. 1 is a schematic cross-sectional view of a conventional flexible membrane cMUT 10, which has a fixed substrate 101 having a bottom electrode 120, flexible membrane 110 connected to the substrate 101 through membrane supports 130, and movable top electrode 150. The flexible membrane 110 is spaced from the bottom electrode 120 by the membrane supports 130 to form a transducing space 160.

FIG. 2 is a schematic cross-sectional view of embedded-spring cMUT (ESCMUT) 200, which is described in the PCT International Application No. PCT/IB2006/051568, entitled MICRO-ELECTRO-MECHANICAL TRANSDUCERS, filed on May 18, 2006; and International Application (PCT) No. PCT/IB2006/051569, entitled MICRO-ELECTRO-MECHANICAL TRANSDUCERS, filed on May 18, 2006, particularly the cMUTs shown in FIGS. 5A-5D therein. The cMUT 200 has a substrate 201, on top of which is spring anchor 203 supporting a spring layer 210; a surface plate 240 connected to the spring layer 210 through spring-plate connectors 230; and a top electrode 250 connected to the surface plate 240. The cMUT 200 may be only a portion of a complete cMUT element (not shown).

Although structurally and mechanically very different, cMUTs 100 and 200 in FIGS. 1-2, and most other cMUTs, can be commonly represented by a simplified schematic model. FIG. 3A shows a simplified schematic cMUT model 300 which shows capacitor 310 consisting of fixed electrode 310a and movable electrode 310b, which is connected to equivalent springs 320 anchored by spring anchors 330. The fixed electrode 310a and the mobile electrode 310b define transducing space 360 therebetween. The electrodes 310a and 310b are connected to an interface circuit 380. The cMUT model can be further simplified as a circuit model having a variable capacitor as shown in FIG. 3B. The variable capacitor 310 in FIG. 3B has two electrodes 310a and 310b and is connected to the interface circuit 380. Essentially all cMUTs based on a variable capacitor, even comb driver cMUTs in which the movable electrode is laterally displaced (along the direction of the electrode surface), may be represented by the variable capacitor model 300 shown in FIG. 3B. In this description, the variable capacitor model 300 shown in FIG. 3B is be used to represent any cMUT regardless of its structural and mechanical characteristics.

Usually a cMUT is biased with a DC voltage either directly or through a bias circuit. The cMUT also connects to an interface circuit, which usually comprises a switch, a transmission (TX) port and a reception (RX) port. In transmission, a signal is applied on the cMUT to transmit the acoustic energy into the medium through the transmission port. In reception, acoustic energy impinging on the cMUT is detected electrically by an interface circuit through the reception port. The switch switches the connection of the cMUT to either transmission port or reception port during operation.

Since the cMUT is a capacitive device, there is low cut-off in frequency response of the cMUT. Thus the cMUT is an inefficient device at low frequency ranges. Moreover, the cMUT itself also need further improvement in reception sensitivity.

SUMMARY OF THE DISCLOSURE

This application discloses a capacitive micromachined ultrasonic transducer (cMUT) system using a modulation technique to increase cMUT sensitivity and for other benefits. Both the modulation method and cMUT systems implementing the modulation method are described.

One aspect of the disclosure is a modulation technique used in a cMUT system at a reception mode for detecting pressure signals such as ultrasonic waves impinging on the cMUT. The higher frequency of the AC carrier signal carries the real signal to a high frequency range to increase the output current signal level. The real signal is later recovered by demodulation. The technique is applicable in both the reception mode and the transmission mode. The AC carrier signal may preferably have an optimal frequency at which the AC carrier signal suffers an optimally low level of signal degradation passing through the cMUT system.

Another aspect of the disclosure is a modulation technique used in a cMUT system at a transmission mode for transmitting an ultrasonic signal to a medium. The method applies to the cMUT a transmission input signal having a transmission frequency and an AC modulation signal having a carrier frequency. The carrier frequency is higher than the transmission frequency. The method allows, in one embodiment, a half-frequency application in which the transmission frequency is about half of an operating frequency of the cMUT. This reduces the high frequency harmonic effect in the cMUT operation. The method also allows more freedom for adjusting the DC bias pressure exerted on the cMUT electrodes. In one embodiment, no DC bias signal is applied, and the DC pressure is contributed by the AC modulation signal.

This disclosure also describes cMUT systems of various designs of modulation signal port, transmission input signal port, reception signal port, demodulator, and band-pass filters. One aspect of the disclosure is a cMUT system having an inductive device connected to the cMUT for tuning impedance of the cMUT. Benefited by the high frequency of the carrier signal in the modulation technique, the inductive device for tuning may have very low inductance and therefore may be micromachined on a substrate. In addition, the bandwidth degradation caused by impedance tuning is minimized. This enables a cMUT system having a cMUT array and an inductive device array, both micromachined on a respective substrate, either wire-bonded or directly bonded to form a complete cMUT system.

DETAILED DESCRIPTION

Figure 1:
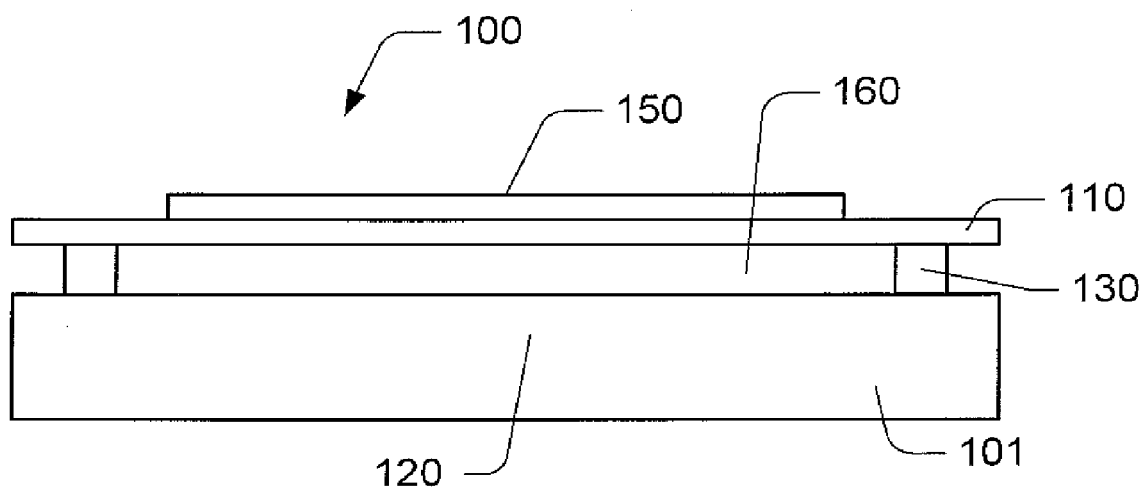
FIG. 1 is a schematic cross-sectional view of a conventional flexible membrane cMUT.
Figure 2:
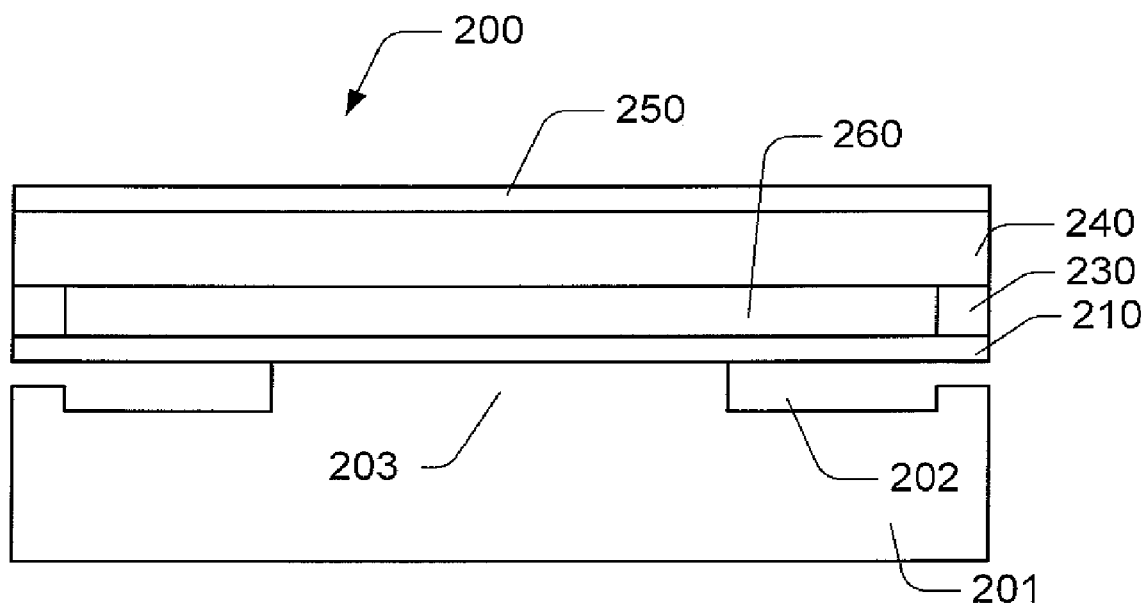
FIG. 2 is a schematic cross-sectional view of embedded-spring cMUT (ESCMUT).
Figure 3A:
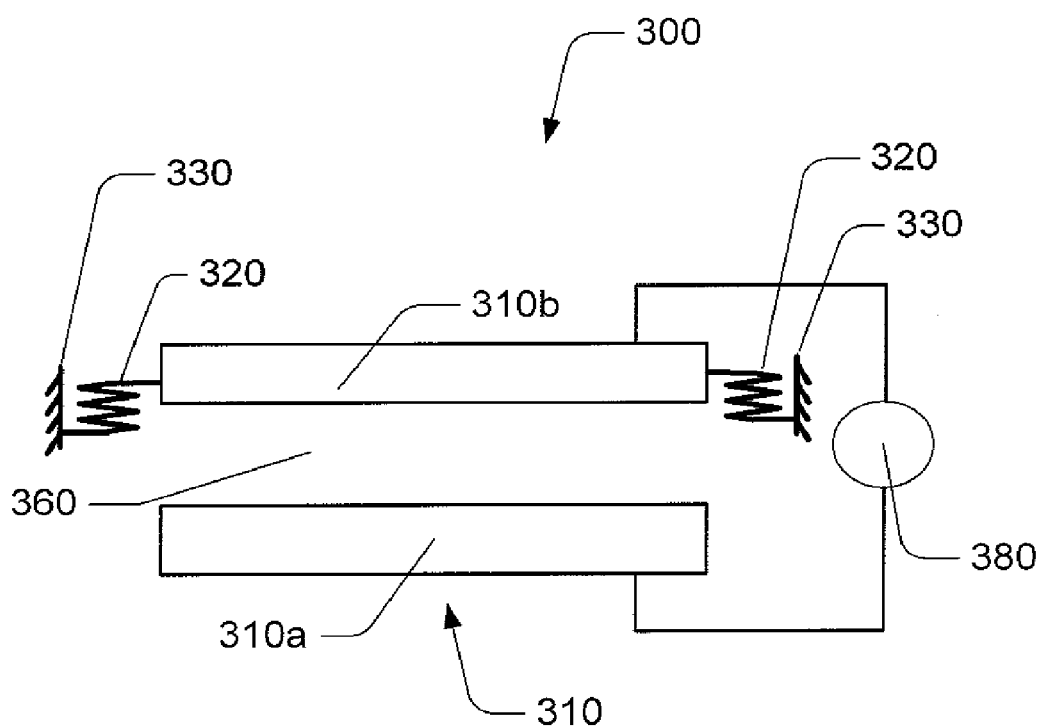
FIG. 3A shows a simplified schematic cMUT model.
Figure 3B:
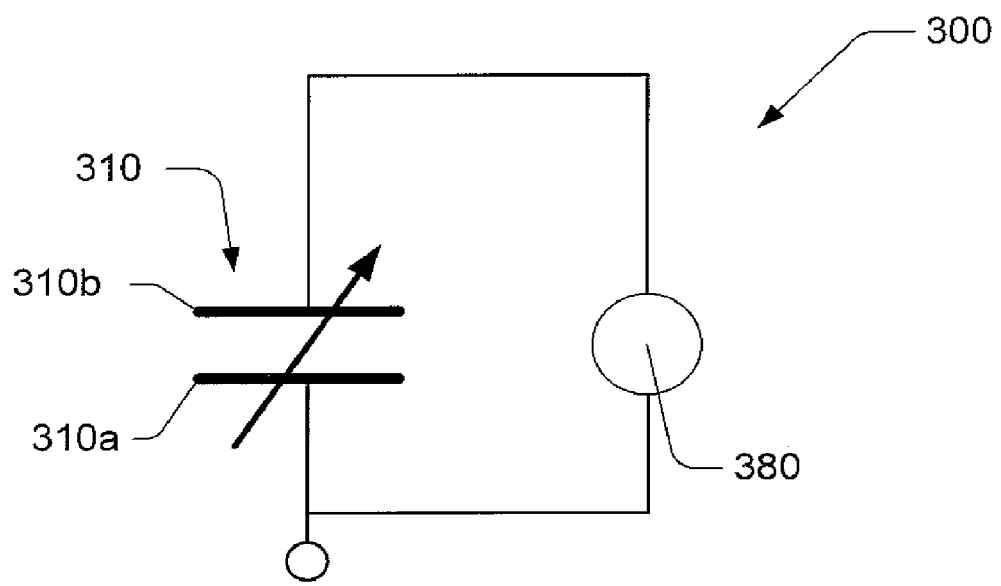
FIG. 3B shows a further simplified cMUT representation as a circuit model having a variable capacitor.

The cMUT with modulation and the modulation methods for operating a cMUT are described in detail along with the figures, in which like parts are denoted with like reference numerals or letters. The methods are adapted for transmitting an ultrasonic signal and/or receiving a pressure signal using a cMUT system.

The method uses an AC modulation signal to perform modulation in cMUT operation. The AC modulation signal may either include a carrier signal (Vcarrier) only or the carrier signal plus a DC bias (Vcarrier+Vdc). The modulation fundamentally changes the way to operate a cMUT, including the signal process, and offers a number of potential advantages over the existing cMUT operation using the DC bias only without modulation.

In this description, a cMUT is represented by a variable capacitor. Any cMUT that is functionally equivalent to a variable capacitor, or can be substantially represented by a variable capacitor, can be used in the systems and methods described herein, regardless of the specific structure and mechanics of the cMUT.

cMUT System with Modulation Signal

Figure 4A:
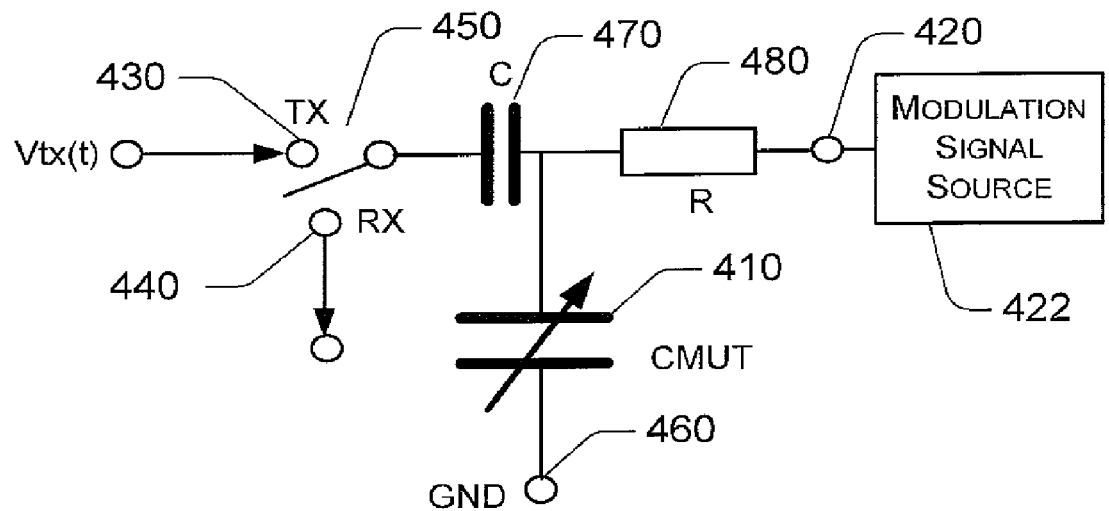
FIG. 4A shows a first exemplary cMUT with modulation in operation.

FIG. 4A shows a first exemplary cMUT with modulation in operation. The setup includes cMUT 410 which is represented by a variable capacitor. One electrode of the cMUT 410 is connected to modulation signal port 420, transmission (TX) port 430 and reception (RX) port 440 through a bias circuit which includes capacitor 470 and resistor 480. Switch 450 is used to switch the line between the transmission port 430 and the reception port 440. Both the bias circuit (including the capacitor 470 and the resistor 480) and the switch 450 are connected to the same electrode of the cMUT 410. The other side of the cMUT 410 is connected to electrical ground 460.

A modulation signal is generated by modulation signal source 422 and applied at the modulation signal port 420, which may be a separate port, a port integrated with the cMUT 410, or a port integrated with the modulation signal source 422. The detail of the modulation signal, modulation, and demodulation will be described later in this description.

In transmission mode, the switch 450 is switched to the transmission port 430 (TX). A transmission (TX) signal Vtx (t) is applied to the cMUT system at the transmission port (TX) 430. The cMUT 410 responds to the transmission (TX) signal Vtx(t) and the modulation signal (Vcarrier plus an optional Vdc), which are applied to the cMUT 410 at the same time, and generates an ultrasonic wave in the medium (not shown) in which the cMUT 410 is placed. The transmission mode may also be used as an actuation mode in which the cMUT generates a motion of its movable electrode in response to the transmission input signal Vtx(t) and the modulation signal (Vcarrier plus the optional Vdc). The motion of the movable electrode can be used for actuating a component which is either directly connected to the movable electrode or indirectly connected to the movable electrode through a medium. The transmission mode or actuation mode using modulation is described further in detail in later sections of this description.

In reception mode, the pressure signal (such as a pressure generated by an impinging ultrasonic wave) is applied to a movable electrode of the cMUT 410 to cause a motion of the movable electrode. The motion of the movable electrode generates a capacitance change of the cMUT 410. The capacities change and the voltage applied at the cMUT 410 cause an electric current signal, which is received at the reception port (RX) 440. The voltage applied at the cMUT 410 includes the modulation signal Vcarrier and the optional Vdc. The reception mode using modulation is described further in detail in later sections of this description.

Figure 4B:
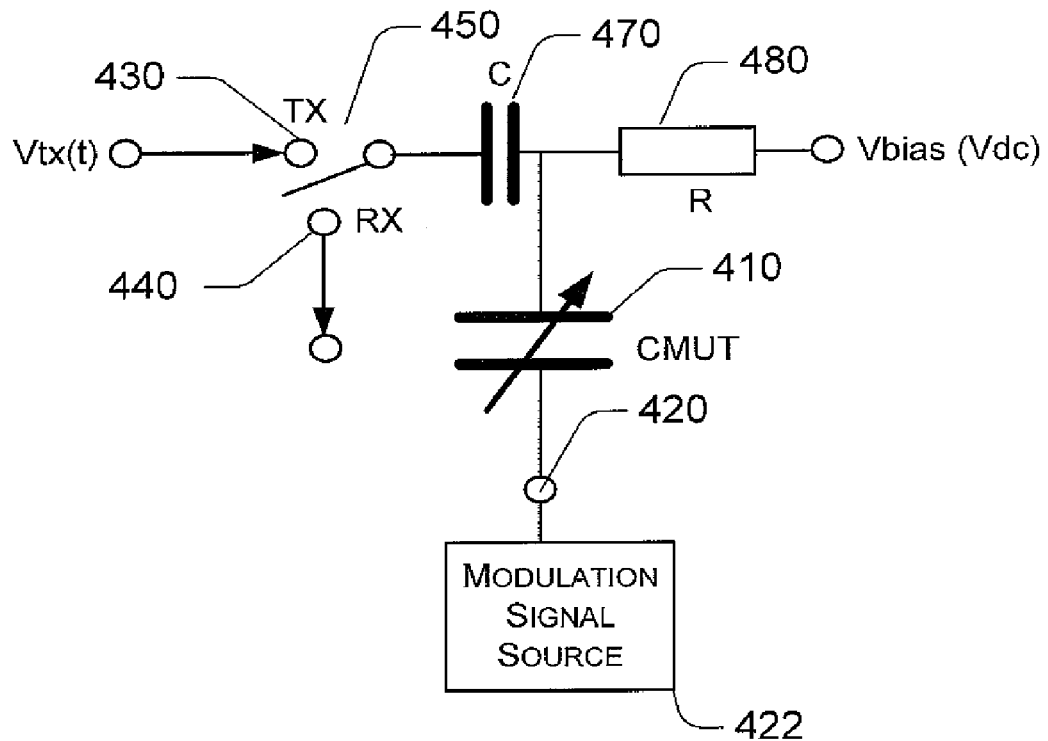
FIG. 4B and FIG. 4C show two exemplary variations of the cMUT system of FIG. 4A.
Figure 4C:
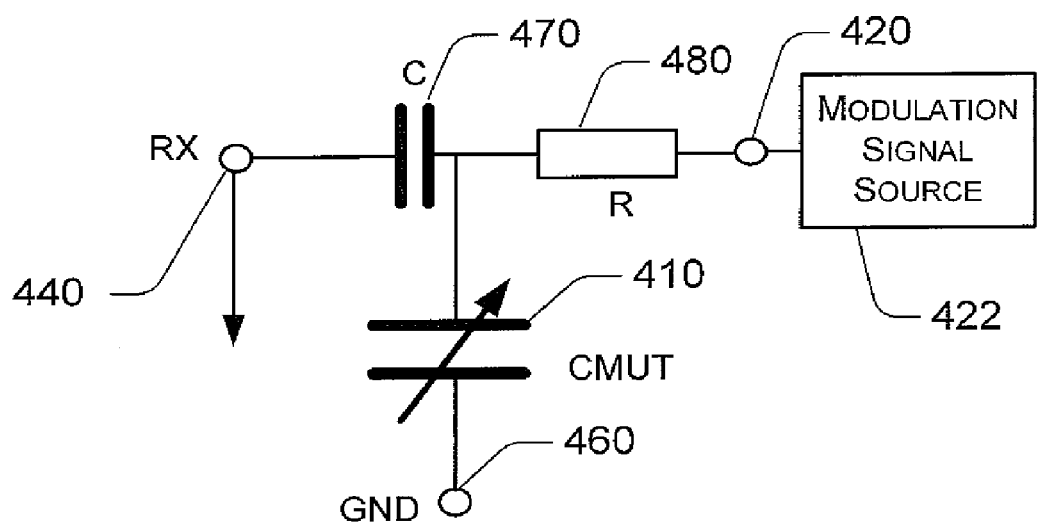

Various modifications of the cMUT system of FIG. 4A may also be used. FIG. 4B and FIG. 4C show two exemplary variations of the cMUT system of FIG. 4A. In FIG. 4B, the modulation signal source 422 and the modulation port 420 are connected to the opposite electrode of the cMUT, instead of being connected to the same electrode of the cMUT as the transmission port 430 and the reception port 440 as that in FIG. 4A. In addition, a DC bias Vdc is applied to the cMUT through resistor 480. In FIG. 4C, the cMUT system only has a reception port (RX) 440 but no transmission port. Accordingly, no switch is needed. Such a cMUT system would work as a receiver or sensor only, and would be useful for applications such as ultrasonic sensing and photo-acoustic imaging.

Figure 5:
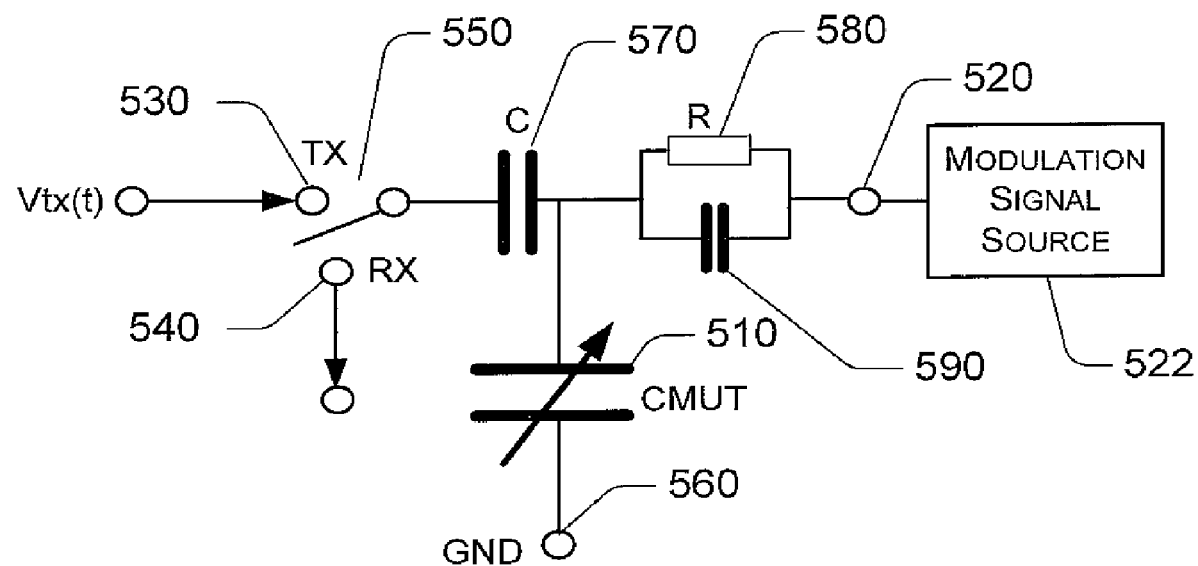
FIG. 5 shows a second exemplary cMUT with modulation in operation.

FIG. 5 shows a second exemplary cMUT with modulation in operation. The cMUT system of FIG. 5 is similar to that of FIG. 4 except for a different bias circuit used. The cMUT system includes cMUT 510 which is represented by a variable capacitor. One electrode of the cMUT 510 is connected to modulation signal port 520, transmission (TX) port 530 and reception (RX) port 540 through a bias circuit which includes capacitor 570, resistor 580 and additional capacitor 590. The additional capacitor 590 is in parallel with the resistor 580. Switch 550 switches the line between the transmission port 530 and the reception port 540. Both the bias circuit (capacitor 570, resistor 580, and additional capacitor 590) and the switch 550 are connected to the same electrode of the cMUT 510. The other side of the cMUT 510 is connected to electrical ground 560.

A modulation signal is generated by modulation signal source 522 and applied at the modulation signal port 520. A transmission (or actuation) TX signal Vtx (t) is applied to the cMUT system at the transmission port (TX) 530. The transmission mode and the reception mode work in a similar manner to that in the cMUT system of FIG. 4.

Figure 6:
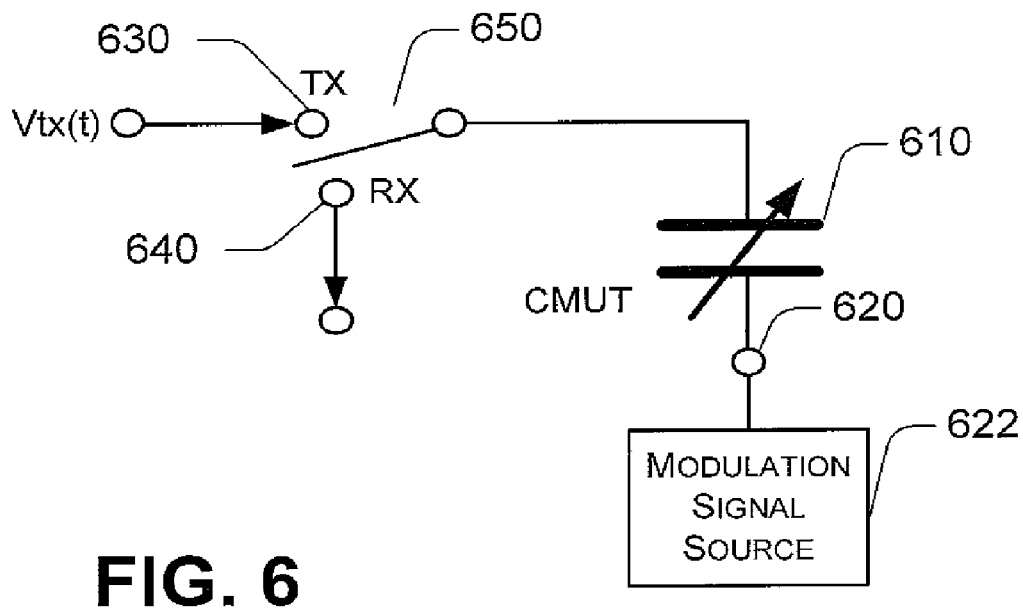
FIG. 6 shows a third exemplary cMUT with modulation in operation.

FIG. 6 shows a third exemplary cMUT with modulation in operation. In this cMUT system, transmission port (TX) 630, reception port (RX) 640 and switch 650 are connected to one electrode of cMUT 610, while modulation signal port 620 is connected to the other electrode of the cMUT 610. The transmission port 630 and reception port 640 connect to the cMUT 610 through the switch 650. The modulation signal port 620 is connected to the cMUT 610 directly. A modulation signal is generated by modulation signal source 622 and applied at the modulation signal port 620. A transmission or actuation TX signal Vtx (t) is applied to the cMUT system at the transmission port (TX) 630. The transmission mode and the reception mode work in a similar manner to that in the cMUT of FIG. 4.

Figure 7:
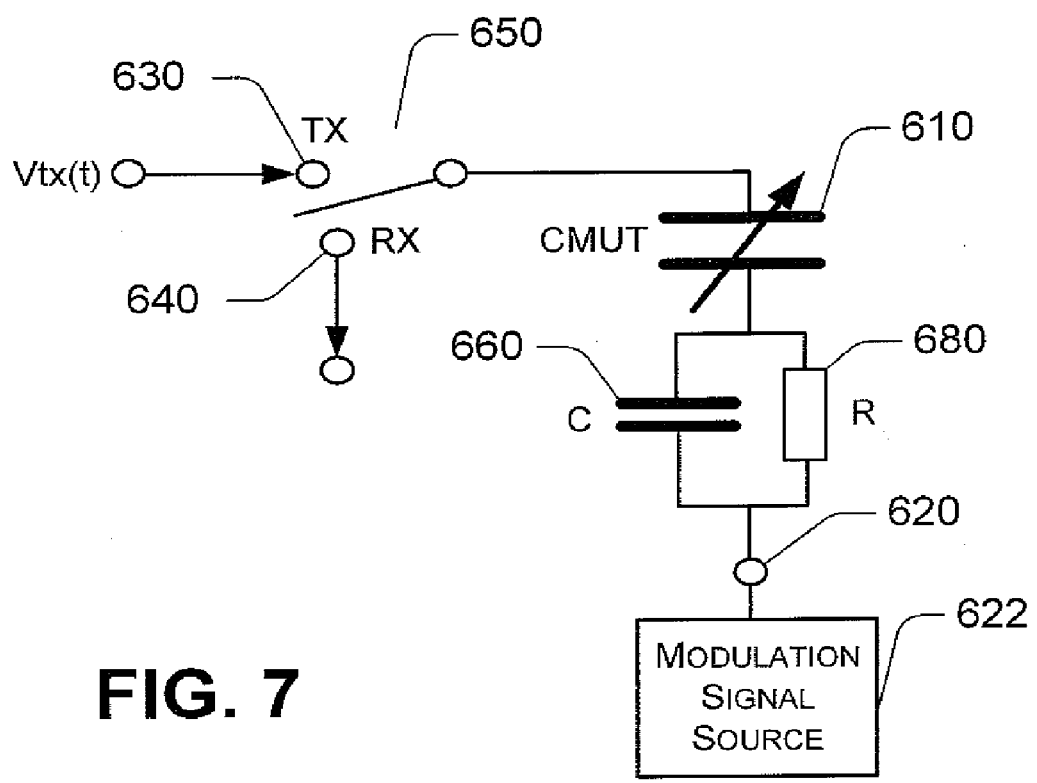
FIG. 7 shows a fourth exemplary cMUT with modulation in operation.

FIG. 7 shows a fourth exemplary cMUT with modulation in operation. The cMUT system of FIG. 7 is similar to that of FIG. 6 except that the modulation port 720 is connected to cMUT 710 through a shorting protection circuit, which includes a capacitor 670 and a parallel resistor 680.

Figure 8A:
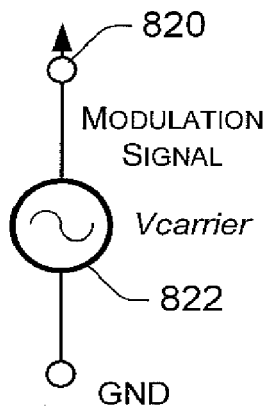
FIGS. 8A, 8B and 8C show several exemplary modulation signals that may be used in the cMUT systems with modulation implemented.
Figure 8B:
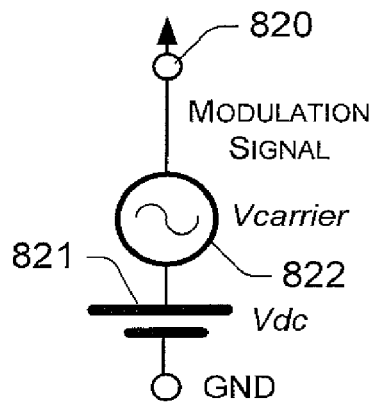
Figure 8C:
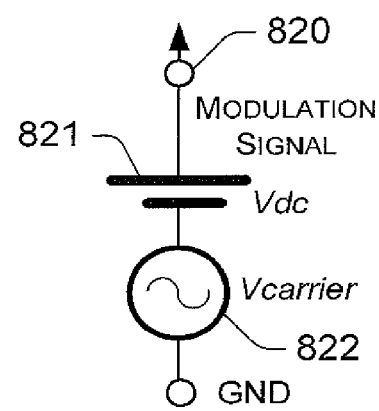

FIGS. 8A, 8B and 8C show several exemplary modulation signals that may be used in the cMUT systems of FIGS. 4-7. In FIG. 8A, the modulation signal is an AC carrier signal (Vcarrier) generated by an AC signal source 822, and is the only signal applied at modulation signal port 820. In FIG. 8B, the modulation signal has an AC carrier signal (Vcarrier) and a DC bias (Vdc) in series. The AC carrier signal (Vcarrier) is generated by AC signal source 822 and directly applied at modulation signal port 820, while the DC bias (Vdc) is provided by DC signal source 821 and applied before the AC carrier signal in series. In FIG. 8C, the modulation signal has an AC carrier signal (Vcarrier) and a DC bias (Vdc) in series. The DC bias (Vdc) is directly applied at modulation signal port 820, while the AC carrier signal (Vcarrier) is applied before the AC carrier signal in series.

Figure 9:
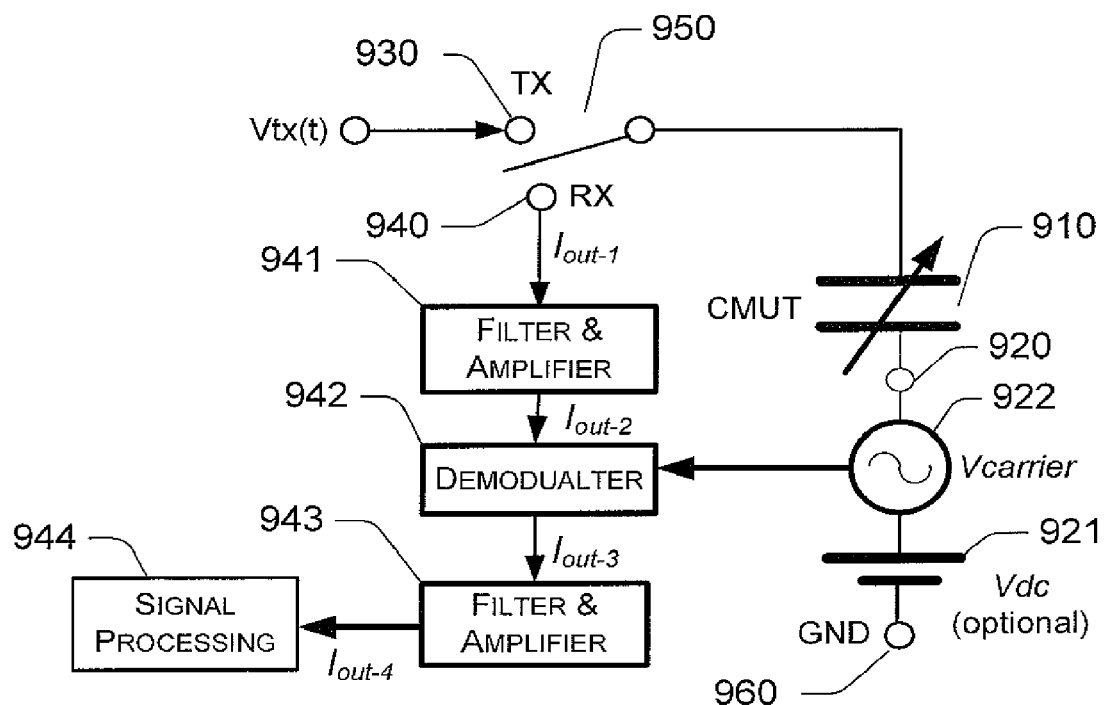
FIG. 9 shows an example of a cMUT system with modulation, band-pass filtering, demodulation and signal processing.

The cMUT systems of FIGS. 4-7 may further include components for signal processing and demodulation as shown in FIG. 9.

FIG. 9 shows an example of a cMUT system with modulation, band-pass filtering, demodulation and signal processing. The exemplary cMUT system of FIG. 9 is based on the cMUT setup of FIG. 6, but the same or similar concept may be applied to other cMUT setups (such as that shown in FIGS. 4A-4C, 5 and 7) as well. In this embodiment, transmission port 930, reception port 940 and switch 950 are connected to one electrode of cMUT 910, while modulation signal port 920 is connected to the other electrode of the cMUT 910. The transmission port 930 and reception port 940 connect to the cMUT 910 through the switch 950. The modulation signal port 920 is connected to the cMUT 910 directly. The modulation signal, which includes an AC carrier signal (Vcarrier) generated by AC signal source 922 and an optional DC bias 921 (Vdc) generated by DC signal source 921, is applied at modulation signal port 920. A transmission or actuation signal Vtx(t) is applied to the cMUT system at the transmission port 930.

For detection, output signal $I_{out-1}$ is received at reception port 940, passes through an amplifier/filter assembly 941 if needed to become output signal $I_{out-2}$, passes through a demodulator 942 to become output signal $I_{out-3}$, and then passes through another amplifier/filter assembly 943 if needed to become output signal $I_{out-4}$. The output signal $I_{out-4}$ is sent to signal process unit 944. To perform modulation on the signal, the demodulator 942 may also be connected to the modulation signal source 922 to receive information of the modulation signal Vcarrier.

The cMUT system of FIG. 9 can be adapted for transmitting an ultrasonic signal and/or receiving a pressure signal such as impinging ultrasonic waves. The transmission mode and the reception mode work in a similar manner to that in the cMUT system of FIG. 4.

Modulation

The modulation method is discussed in detail in following paragraphs with figures. In transmission operation (TX) using modulation, the voltage applied on a cMUT system (e.g., the cMUT system of FIG. 9) is:

$$V_{in}=Vdc+V\text{carrier}(t)+Vtx(t), \quad (1)$$

where Vdc is optional DC bias, Vcarrier is the modulation signal and Vtx is the transmission/actuation TX signal applied by the system. The electrostatic pressure generated by the cMUT is proportional to $V_{in}^2$ as follows:

$$\text{pressure} \propto V_{in}^2 = (Vdc+V\text{carrier}(t)+Vtx(t))^2 = Vdc^2 + V^2\text{carrier}(t)+V^2tx(t)+2VdcVtx(t)+2VdcV\text{carrier}(t)+2Vtx(t)V\text{carrier}(t) \quad (2)$$

The above $V_{in}^2$ can be schematically expressed in the frequency domain as described below with the references to FIGS. 10-11.

Figure 10:
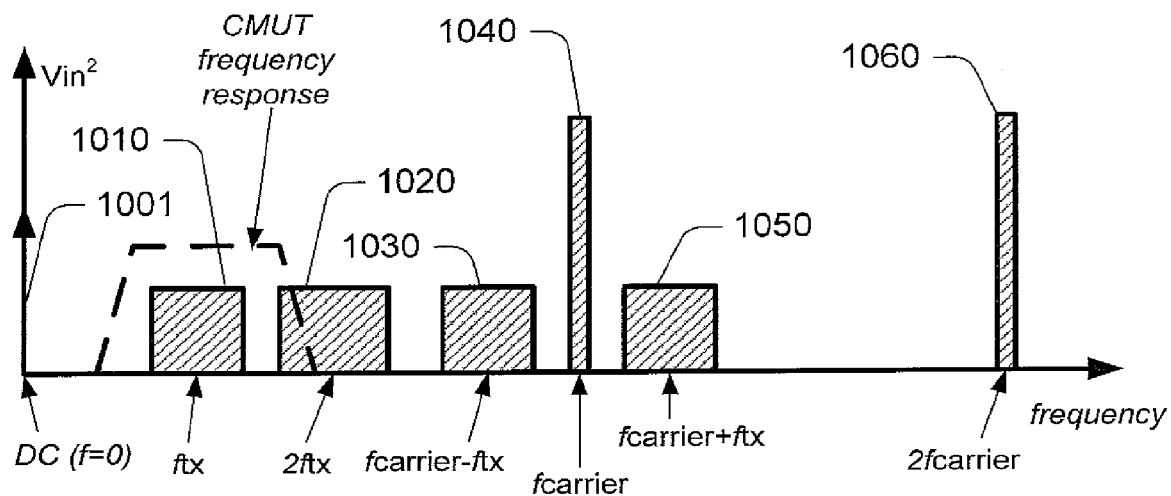
FIG. 10 is a diagrammatic illustration of the components of cMUT pressure ($\propto V_{in}^2$) in the frequency domain.

FIG. 10 is a diagrammatic illustration of the components of $V_{in}^2$ in the frequency domain. As shown in FIG. 10, the frequency components in $V_{in}^2$ include the following:

DC component 1001, which is contributed by the $Vdc^2$ term, and also by the zero-frequency elements of the Vcarrier(t)$^2$ and Vtx(t)$^2$ terms in the above equation;

ftx component 1010, at the cMUT transmission frequency ftx (operation frequency for transmission), and contributed by 2VdcVtx(t) term in the above equation;

2 ftx component 1020, at a double cMUT operation frequency 2 ftx for transmission (TX), and contributed by the $V^2$tx(t) term;

fcarrier−ftx component 1030, at a frequency fcarrier−ftx which is the differential frequency between the carrier signal Vcarrier and the cMUT operation frequency ftx for transmission (TX), and contributed by the 2Vtx(t)Vcarrier(t) term;

fcarrier component 1040, at the frequency fcarrier of the carrier signal Vcarrier, and contributed by the 2VdcVcarrier(t) term;

fcarrier+ftx component 1050, at a frequency fcarrier+ftx which is the sum of frequency fcarrier of the carrier signal Vcarrier and the cMUT operation frequency ftx for transmission (TX), and also contributed by the 2Vtx(t)Vcarrier(t) term; and 2fcarrier component 1060, at a double frequency 2fcarrier of the carrier signal Vcarrier, and contributed by the $V^2$carrier(t) term.

It is noted that in this description, when a signal (voltage signal, current signal or pressure signal) is said to have a certain frequency, there is no suggestion that signal is limited to a pure sine wave signal having a single frequency, but only means that the signal has a component characterized by that frequency. In some situations, the signal may have a dominant component characterized by that frequency, but such dominance of a single frequency is not required. For example, the individual frequency components as illustrated in the present description may not each correspond to a pure sine wave signal having a single frequency, but rather just be a superposition of signals of frequencies concentrated in a range of frequencies centered around that frequency.

Amplitudes of $Vdc^2$, Vcarrier(t)$^2$ and Vtx(t)$^2$ terms all contribute to DC component 1001 in $V_{in}^2$. The DC component 1001 in $V_{in}^2$ may be used to set the cMUT operation point.

Even though $V_{in}^2$ has many frequency components, the cMUT itself has a limited bandwidth. The cMUT thus behaves as a band-pass filter such that only those frequency components that are in the cMUT frequency band contribute to the output pressure efficiently.

Figure 11:
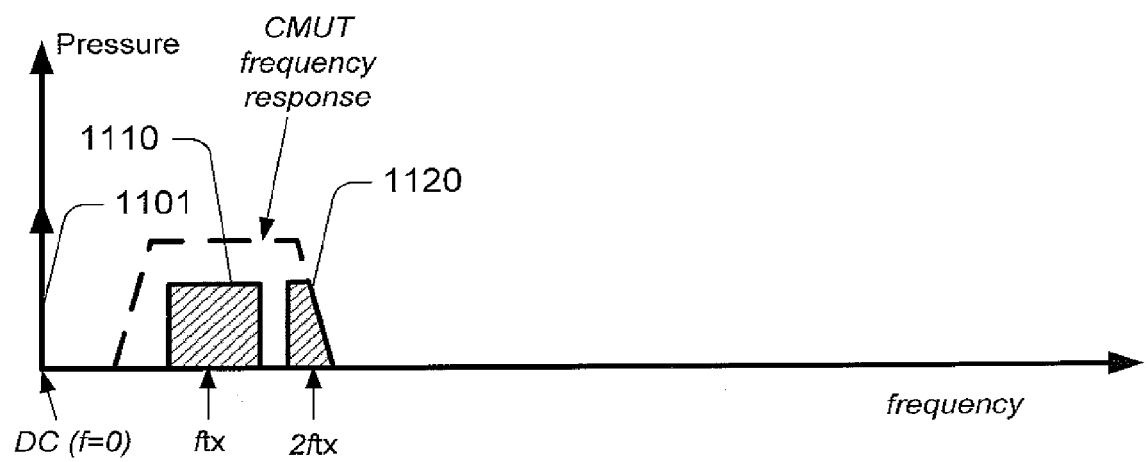
FIG. 11 is a diagrammatic illustration of the band-pass filter effect of a cMUT having a limited frequency response bandwidth.

FIG. 11 is a diagrammatic illustration of the band-pass filter effect of a cMUT having a limited frequency response bandwidth. In this example, only the ftx component 1110 and a part of the 2fx component 1120 actually contribute to the generation of the output pressure.

Therefore, given the filter effect of the cMUT frequency response, the output pressure can be written as:

$$\text{Pressure} \propto V_{in}^2 \propto Vdc^2 + V\text{carrier}^2(f=0) + 2VdcVtx(t) + Vtx(t)^2, \quad (3)$$

where Vcarrier$^2$(f=0) represents the zero-frequency element of the Vcarrier$^2$ component.

The frequency components contributing to be output pressure as shown in FIG. 11 have a similarity to those of a cMUT using a conventional DC bias. However, the modulation method described herein has several new characteristics as described below.

First, the modulation method provides more freedom to set the DC term since the DC term may be controlled by the amplitudes of all input signals $Vdc^2$, Vcarrier(t)$^2$ and Vtx(t)$^2$. For example, Vdc may be chosen to be zero, while the amplitude of the carrier signal Vcarrier may be carefully selected to result in a desired DC bias pressure on the cMUT.

Second, the Half-Frequency method and Absolute-Value Signal method as described in the U.S. patent application Ser. No. 11/695,919, entitled "SIGNAL CONTROL IN MICRO-MACHINED ULTRASONIC TRANSDUCER", filed on Apr. 3, 2007 by the common applicant are also applicable in this modulation-based transmission/actuation method to reduce the harmonic in the output pressure. For example, if Vtx(t)=$V_{p-p}$abs(sin($\omega$t/2)) and Vdc=0, then $$\text{Pressure} \propto V_{in}^2 \propto \left(\frac{V_{carrier}^2}{2} + \frac{V_{p-p}^2}{2}\right) - \frac{V_{p-p}^2}{2}\cos(\omega t). \quad (4)$$

That is, using a transmission input signal having a half frequency ($\omega$/2) of the cMUT operating frequency ($\omega$), the output pressure of the cMUT responses at the cMUT operating frequency ($\omega$) without significant contributions by the higher frequency harmonic components. At the same time, the amplitude of the Vcarrier signal contributions to the zero-frequency component $$\frac{V_{carrier}^2}{2} + \frac{V_{p-p}^2}{2}$$

to make the static bias pressure independently adjustable. Without the Vcarrier signal, the zero-frequency component in the pressure would be singularly determined by the amplitude of the transmission term $$\frac{V_{p-p}^2}{2}\cos(\omega t)$$

and therefore could not be independently adjusted, unless a nonzero Vdc is applied.

In reception operation (TX) using the modulation method, the pressure signal (e.g., an impinging acoustic wave) generates a capacitance change in the cMUT. Together with the voltage applied on the cMUT, the capacities change results in an output current signal. The output current generated by the cMUT from the pressure signal (e.g., the impinging acoustic wave) may be written as:

$$I_{out} = \frac{\partial}{\partial t} Q = \frac{\partial}{\partial t}(CV),$$

where C is the capacitance of the cMUT, and can be written as:

$$C = C_0 + Crx(t),$$

where $C_0$ is nominal capacitance and Crx(t) is the capacitance change of the cMUT.

V is voltage applied on the cMUT, and can be written as:

$$V = Vdc + V\text{carrier}(t),$$

where Vdc is optional. Therefore, $$I_{out} = V_{dc}\frac{\partial}{\partial t}C_{rx}(t) + C_0\frac{\partial}{\partial t}V_{carrier}(t) + \frac{\partial}{\partial t}(C_{rx}(t)V_{carrier}(t)). \quad (5)$$

Figure 12:
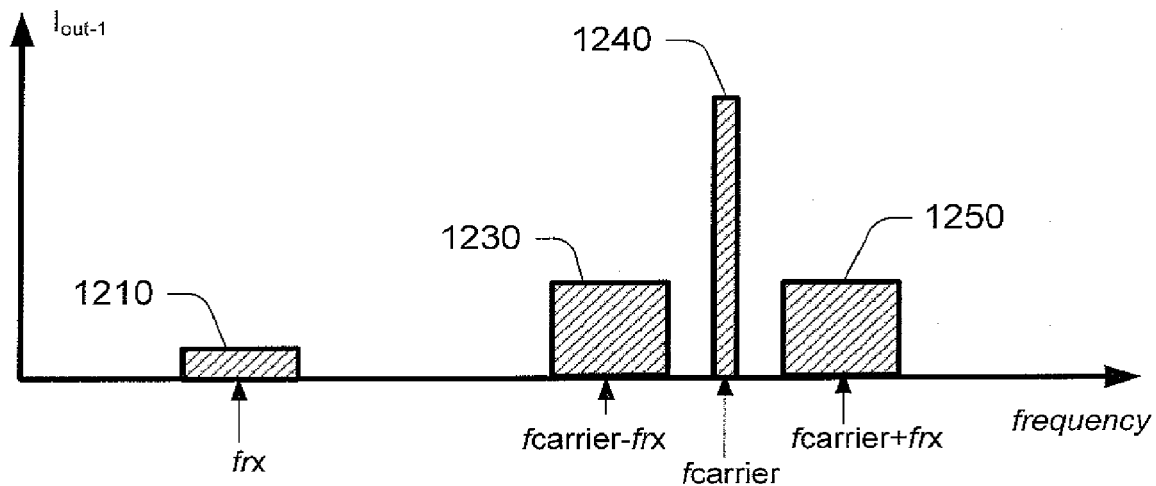
FIG. 12 shows the frequency components of the current output $I_{out-1}$ from the cMUT in reception mode (RX).

FIG. 12 shows the frequency components of the current output $I_{out\text{-}1}$ from the cMUT in reception mode (RX). As shown in FIG. 12, the current output $I_{out\text{-}1}$ has following components:

frx component 1210 at frequency frx, which is a non-modulated component at the frequency of the pressure signal (e.g., the ultrasonic signal impinging on the cMUT) during reception (RX) operation, contributed by the term $$V_{dc}\frac{\partial}{\partial t}C_{rx}(t)$$

in above equation of current output $I_{out}$;

fcarrier component 1240 at frequency fcarrier, which is the non-modulated carrier component at the frequency of the carrier signal Vcarrier; contributed by the term $$C_0\frac{\partial}{\partial t}V_{carrier}(t)$$

the above equation;

fcarrier−frx component 1230 and fcarrier+frx component 1250, which are modulated components both contributed by the term $$\frac{\partial}{\partial t}(C_{rx}(t)V_{carrier}(t))$$

in the above equation.

The fcarrier−frx component 1230 and fcarrier+frx component 1250 are modulated components containing a modulated carrier signal carrying information of the pressure signal (e.g., an ultrasonic signal) sensed by the cMUT 910. Since the output current Iout is proportional to the signal frequency, the modulated fcarrier−frx component 1230 and fcarrier+frx component 1250 are greater than the non-modulated component frx which is at a lower frequency. As will be shown, in one embodiment the fcarrier−frx component 1230 and fcarrier+frx component 1250 are the only useful signals kept after a band-pass filter, as the non-modulated frx component 1210 may be filtered out. In other words, the non-modulated frx component 1210, which is the useful signal in the conventional cMUT operation methods, may be intentionally abandoned in the modulation method. This is advantageous because the modulated fcarrier−frx component 1230 and fcarrier+frx component 1250 may be much stronger signals than non-modulated frx component 1210 due to their higher frequencies. For example, if the carrier frequency fcarrier is twice as high as the frequency frx of the pressure signal (e.g., the impinging ultrasonic signal), the modulated output current components fcarrier−frx component 1230 and fcarrier+frx component 1250 may also be about twice as high as the non-modulated output current component frx. Therefore, the modulation improves the sensitivity using a carrier signal with a higher frequency. In some preferred embodiments, the carrier frequency fcarrier may be 5-10 times as high as the frequency frx of the pressure signal.

In addition, the non-modulated signal component at frequency frx often suffer parasitic capacitance when the signal is traveling through the cMUT circuit. If the carrier frequency fcarrier is high enough, it potentially may reduce or eliminate the parasitic capacitance problem.

The modulation method offers a design freedom for choosing an optimal fcarrier frequency of the modulation signal Vcarrier such that the useful fcarrier−frx component 1230 and fcarrier+frx component 1250 have a higher signal to noise ratio.

As shown in FIG. 9, the reception signal $I_{out}$ may pass a band-pass filter or high pass filter 941 either before or after amplification. The amplification is optional depending on the strength of the signal level.

Figure 13:
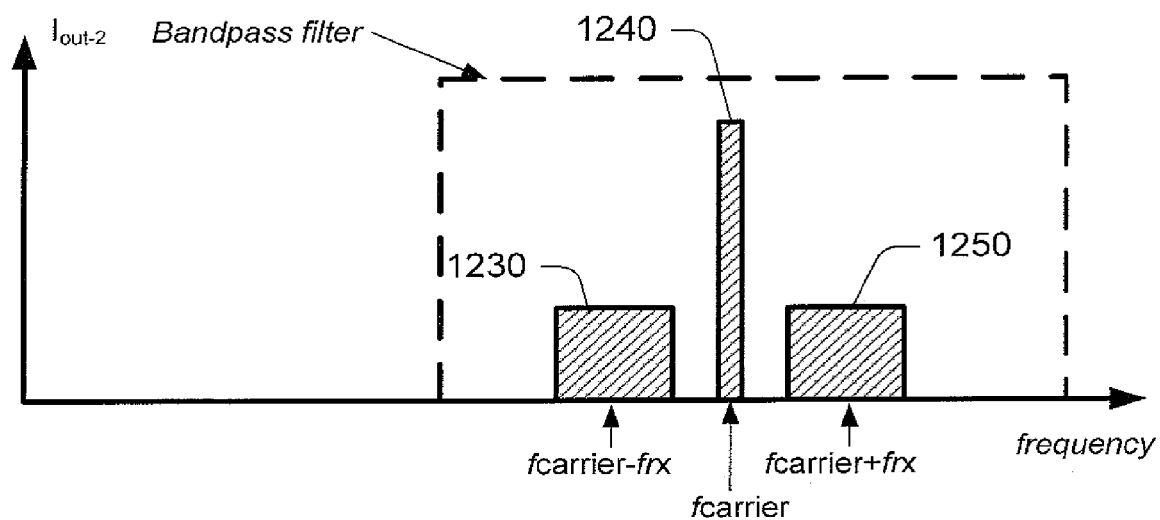
FIG. 13 shows the frequency components of the current output $I_{out-2}$ after the band-pass filter in reception mode (RX).

FIG. 13 shows the frequency components of the current output $I_{out\text{-}2}$ after the band-pass filter 941 (FIG. 9) in reception mode (RX). The frx component 1210 at frequency frx is now filtered out, while the fcarrier component 1240, the fcarrier−frx component 1230 and the fcarrier+frx component 1250 still remain.

The current output signal $I_{out}$ is then demodulated by the demodulator 942 (FIG. 9) using the carrier signal Vcarrier to bring out the useful signals as illustrated below.

Figure 14:
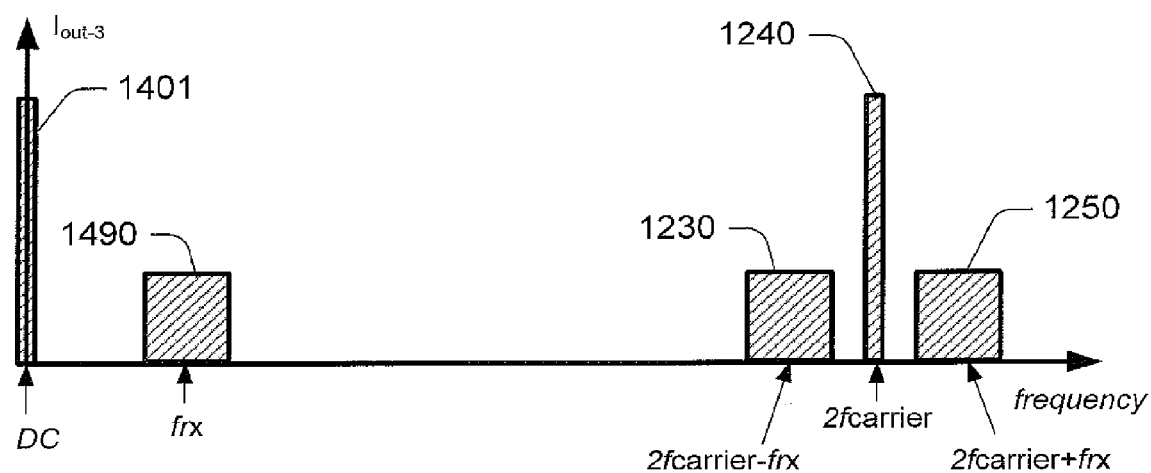
FIG. 14 shows the frequency components of the current output $I_{out-3}$ after demodulation.

FIG. 14 shows the frequency components of the current output $I_{out\text{-}3}$ after demodulation. The demodulation resulted in DC component 1401 and frx component 1490 at frequency frx which is the frequency of the pressure signal (e.g., ultrasonic signal) impinging on the cMUT during RX operation. In other words, the modulation extracts or recovers the real signal frx component 1490 which has been carried by the modulated signals fcarrier−frx component 1230 and the fcarrier+frx component 1250. Unlike the non-modulated frx component 1210 (FIG. 12) in the current output $I_{out}$ immediately after the cMUT 910, the frx component 1490 produced by demodulation has been carried by the fcarrier−frx component 1230 and the fcarrier+frx component 1250 and has a relatively higher signal level.

Figure 15:
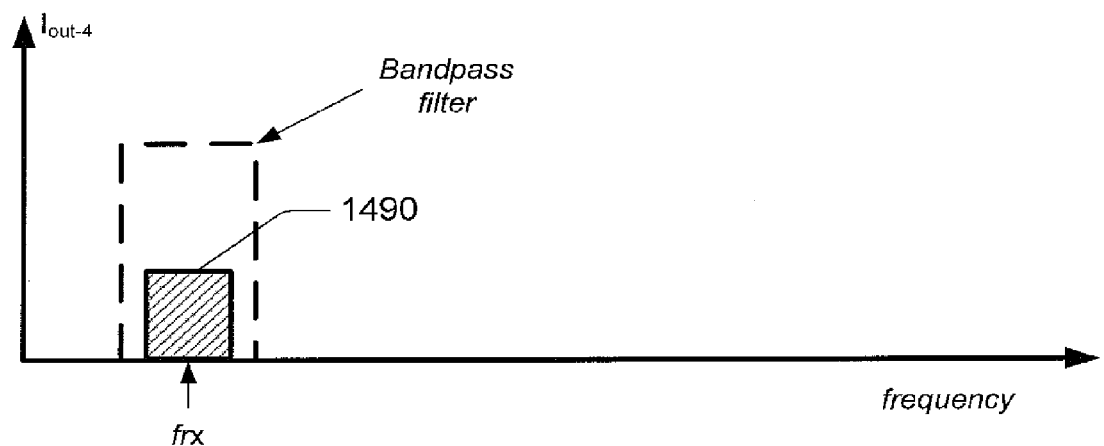
FIG. 15 shows the frequency components of the current output $I_{out-4}$ after a second band-pass or low-pass filter.

FIG. 15 shows the frequency components of the current output $I_{out\text{-}4}$ after band-pass or low-pass filter 943 (FIG. 9). At this stage, the real output signal frx component 1490 at frequency frx is kept. Other high frequency components 1230, 1240 and 1250, and the DC component 1401 are filtered out at this stage using a band-pass or low-pass filter 943. The real output signal frx component 1490 may be then sent to a signal processing unit to complete the reception function of the cMUT system of FIG. 9.

In general, the cMUT output current is higher at higher signal frequencies. The modulation method may increase the cMUT sensitivity by using a carrier signal with a higher frequency to carry the useful signal at a lower frequency until it reaches the demodulation stage 942. The amplification in 941 of FIG. 9 is optional and can be elected if needed.

As has been noted, the cMUT system of FIG. 9 is only used as an exemplary embodiment to illustrate the concept and process of the modulation method. It is appreciated that the modulation method may be used in other cMUT systems, including those shown in other figures herein.

The cMUT bandwidth, especially at lower frequency end, is therefore broadened using the modulation techniques described herein. In addition to increasing the reception sensitivity of the normal cMUT response frequency range, the modulation method may extend the cMUT response bandwidth to a much lower frequencies, even zero-frequency, so that the cMUT may be used to detect the very low-frequency pressure change or even static pressure (e.g., with a pressure change frequency in a range of 0 Hz≦fr≦20 kHz). It is therefore appreciated that the modulation method described herein is not limited to ultrasonic applications where the operating frequency is in the ultrasonic frequency range. At the reception (or sensing) mode, especially, the cMUT may be used as a pressure sensor to detect a pressure signal of very low frequencies, even static pressure.

Impedance Matching and Tuning

In addition to increasing the cMUT sensitivity by shifting frequency to take advantage of high current signal at high frequencies, the modulation method may further increase the cMUT sensitivity through impedance matching/tuning and minimize the impact of impedance tuning on cMUT bandwidth. The modulation method makes the impedance matching/tuning of a cMUT easier than existing systems, and may enable fabrication of new cMUT systems.

Tuning and matching the impedance of a cMUT system may further increase the transducer reception sensitivity. One example of impedance tuning and matching involves tuning the impedance of the transducer to match the impedance of the connection cables interfacing the transducer with signal reception separates. Usually an inductive device (e.g. inductor, transformer, etc.) is used to tune off the capacitance of the transducer.

Given a capacitance C, the inductance L needed to tune the capacitance C is $L=1/j\omega^2 C$. The modulation method described herein raises the cMUT operation frequency $\omega$ to a higher frequency of the carrier signal Vcarrier and therefore makes it possible to use an inductive device (e.g., an inductor or transformer) of smaller inductance to tune the impedance of the cMUT system. In general, the larger the inductance L is, the larger the size of the needed inductive device for tuning. The modulation method therefore enables cMUT impedance tuning using a small inductor. In addition, the transducer bandwidth degradation caused inductor tuning can be minimized because the Q-factor ($Q=1/\omega RC$) is lower at a higher frequency.

If the inductance needed to perform impedance tuning is small enough, it may be possible to use a micromachined inductor or transformer for cMUT impedance tuning. As a result, the inductors or transformers may be integrated with a cMUT array. This may lead to an important benefit for transducer arrays with large number of cMUT elements. For example, a cMUT array and a corresponding tuning inductive device array may be fabricated on the same substrate to achieve direct integration. Alternatively, the cMUT array and the tuning inductor array may be fabricated on two separate substrates, and then assembled together using direct bonding techniques (e.g. eutectic bonding, thermal compression bonding, etc.) or using wire bonding. If the frequency is high enough, the bonding wire itself may serve as an inductor having sufficient inductance to tune the CMUT impedance. In this case, the separate inductors or transformers may not be needed.

Figure 16:
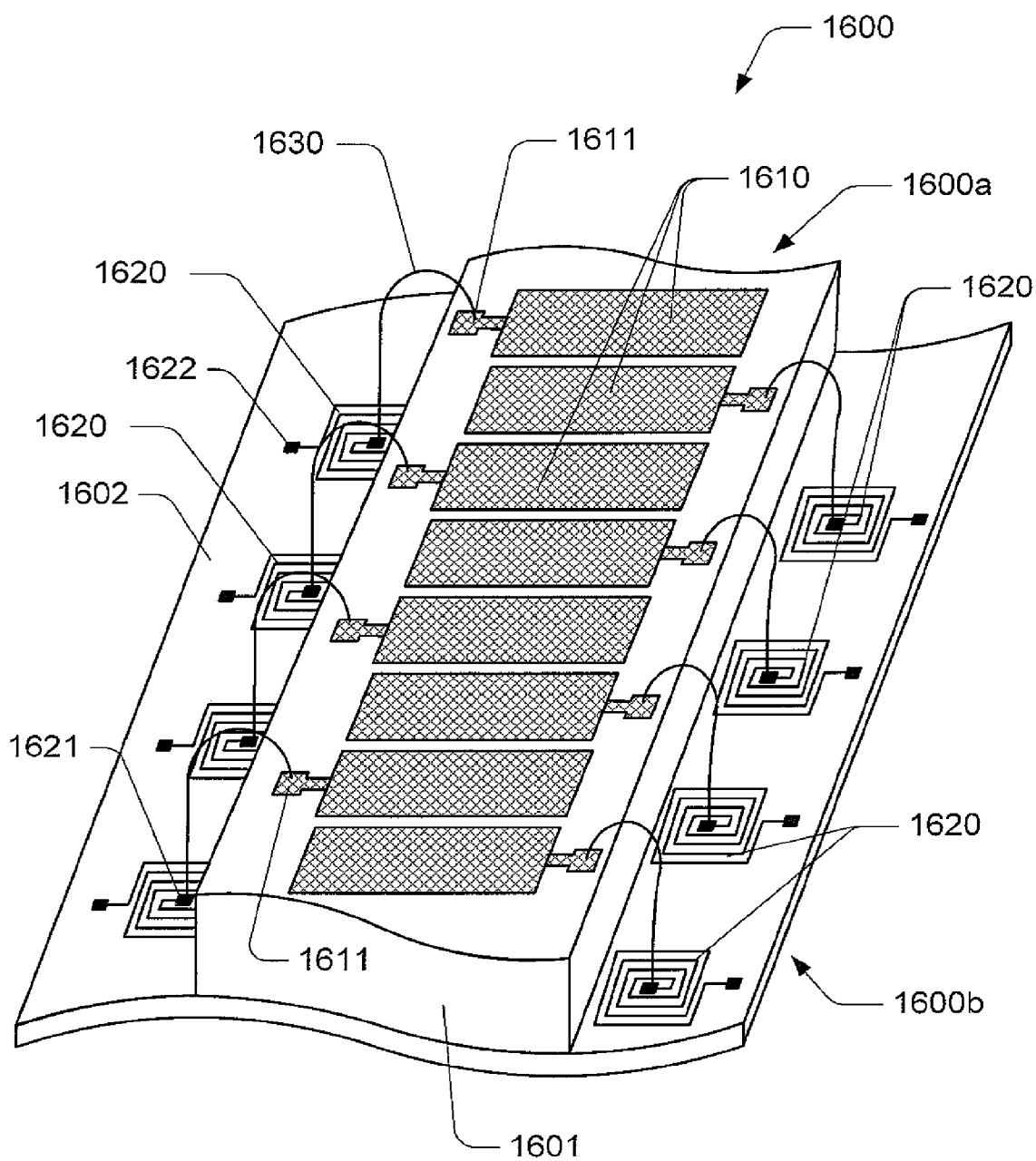
FIG. 16 shows one exemplary cMUT assembly having a cMUT array wire-bonded with an inductive device array.

FIG. 16 shows an exemplary cMUT assembly having a cMUT array wire-bonded with an inductive device array. The cMUT assembly 1600 includes cMUT array 1600a and inductive device array 1600b. The cMUT array 1600 includes cMUTs 1610 built on a substrate 1601, while the inductive device array 1600b includes inductive devices 1620 built on a substrate 1602. The inductive devices 1620 may be any inductive device, such as inductors and transformers, suitable for impedance tuning. The cMUT array 1600a and the inductive device array 1600b are wire-bonded through bonding pads 1611 and 1621. Additional pads 1622 that may be used to interface with the front-end circuit (not shown).

To accomplish impedance matching/tuning, the inductance of the inductive devices 1620 is preferably tuned in the product design and manufacturing stage to achieve a desired matching with the impedance of the cMUTs 1610. Although it is possible to do active tuning in operation, doing so may be too costly and therefore less desired.

Figure 17:
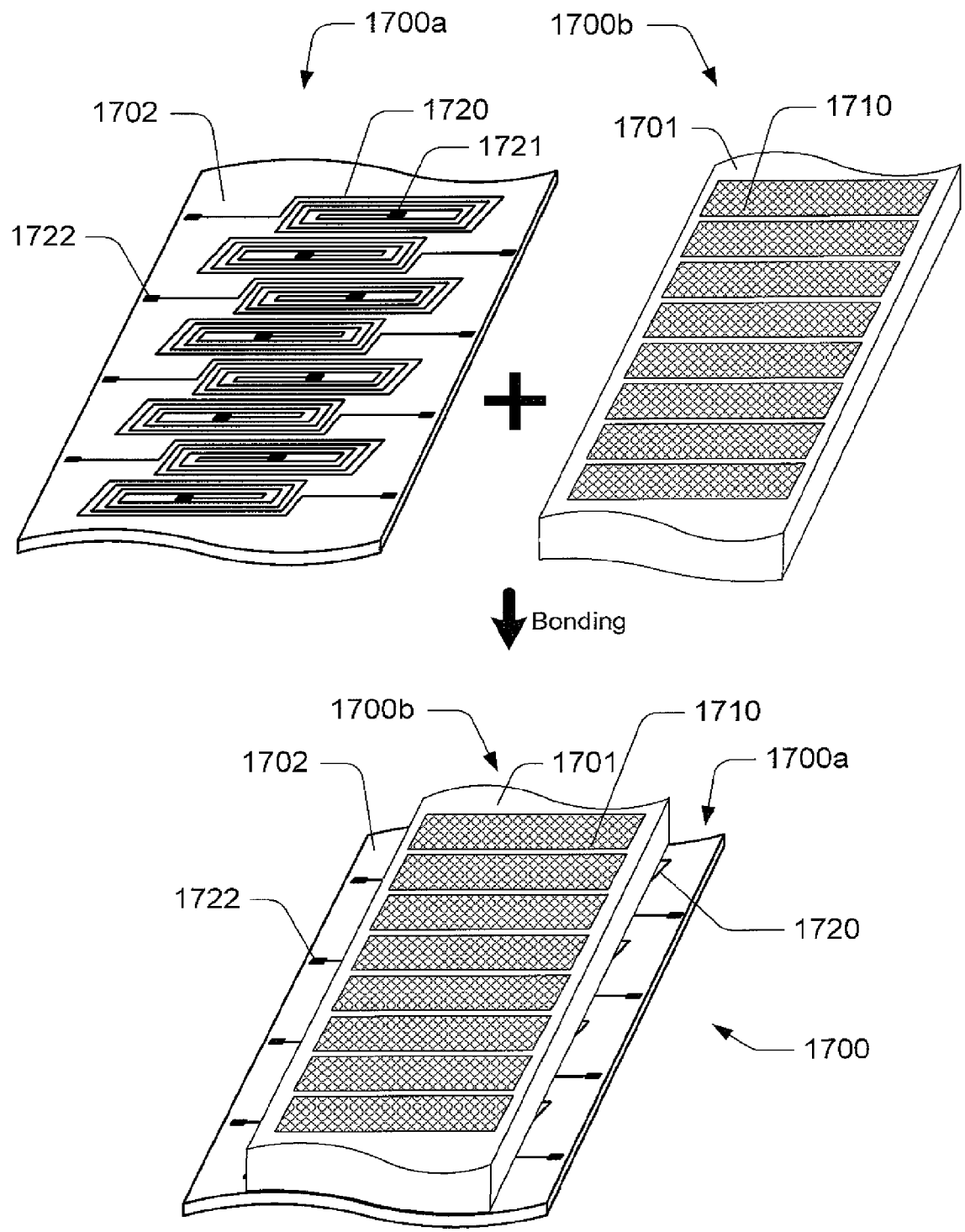
FIG. 17 shows another exemplary assembly of a cMUT array directly bonded with an inductive device array.

FIG. 17 shows another exemplary assembly of a cMUT array directly bonded with an inductive device array. The cMUT assembly 1700 includes cMUT array 1700a and inductive device array 1700b. The cMUT array 1700a includes cMUTs 1710 built on a substrate 1701, while the inductive device array 1700b includes inductive devices 1720 built on a substrate 1702. The inductive devices 1720 may be any inductive device, such as inductors and transformers, suitable for impedance tuning. The cMUT array 1700a and the inductive device array 1700b are directly bonded (without requiring additional wiring) through contact bonding pads on both substrates 1701 and 1702. The contact bonding pads include a first set of contact bonding pads 1721 on inductive device array 1700a, and a second set of the contact bonding pads (not shown) on the backside of the substrate 1701. The two sets of contact bonding pads are aligned with each other to make direct contact to achieve proper binding. Additional pads 1722 may be used to interface with the front-end circuit (not shown). The direct bonding may be done using any suitable method, such as eutectic bonding, thermal compression bonding, etc.

CONCLUSION

The modulation fundamentally changes the way to operate a cMUT, including the signal processing, and offers a number of potential advantages over the existing cMUT operation which uses the DC bias only and has no modulation. The potential benefits of the modulation method include the following:

(1) DC bias voltage is no longer required for cMUT reception operation.
(2) Compared with existing cMUT operation methods, the cMUT reception (RX) signal with modulation is modulated to a higher frequency to increase the cMUT reception sensitivity which it is usually greater at higher frequencies.
(3) The cMUT bandwidth, especially at lower frequency end, is broadened. In addition to increasing the reception sensitivity of the normal cMUT response frequency range, the modulation method may extend the cMUT response bandwidth to a much lower frequencies, even zero-frequency, so that the cMUT may be used to detect the pressure change or the static pressure.
(4) Since the electrical impedance, especially the imaginary part, of the cMUT is a function of signal frequency, the frequency (fcarrier) of the carrier signal can be chosen to produce a desired impedance for the system, for example, to match the impedance of transmission cable. As a result, the device is more efficient to transfer the signal.
(5) A much smaller inductive device (e.g., an inductor or transformer) may be needed to tune the impedance (primarily capacitance) of the cMUT to match the cable capacitance. This makes it possible to fabricate the tuning inductors or transformers using MEMS or IC methods which are more compatible with the fabrication process for making the cMUTs themselves.

(6) The transducer bandwidth degraded by a tuning inductor or transformer may be minimized with modulation method because the method enables the use of inductance of a high Q-factor.

(7) The degradation of noise performance caused by De-Q resistor may also be reduced.

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. A capacitive micromachined ultrasonic transducer (cMUT) system comprising:
    a cMUT having a first electrode and a second electrode;
    at least one of a transmission input signal port and a reception signal port connected to one of the first electrode and the second electrode, wherein the transmission input signal port is adapted for applying a transmission input signal to the cMUT in a transmission mode, and the reception signal port is adapted for receiving an output signal from the cMUT in a reception mode, and wherein the transmission input signal has a non-modulated transmission frequency ftx, and the output signal has a non-modulated reception frequency frx; and
    an AC signal source for generating an AC carrier signal to be applied to the cMUT through a modulation signal port connected to one of the first electrode and the second electrode of the cMUT, wherein the AC carrier signal has a carrier frequency fcarrier which is different from the non-modulated transmission frequency ftx and the non-modulated reception frequency fxr.

2. The cMUT system as recited in claim 1, comprising both the transmission input signal port and the reception signal port, and a port switch to switch between the transmission input signal port and the reception signal port.

3. The cMUT system as recited in claim 1, wherein the modulation signal port and the at least one of the transmission input signal port and the reception signal port are connected to the same electrode of the cMUT.

4. The cMUT system as recited in claim 1, wherein the at least one of the transmission input signal port and the reception signal port are connected to the first electrode of the cMUT, and the modulation signal port is connected to the second electrode of the cMUT.

5. The cMUT system as recited in claim 1, wherein the modulation signal port is directly connected to the one of the first electrode and the second electrode of the cMUT.

6. The cMUT system as recited in claim 1, wherein the modulation signal port is connected to the one of the first electrode and the second electrode of the cMUT through a shorting protection circuit.

7. The cMUT system as recited in claim 1, further comprising a DC signal source for generating a DC bias signal.

8. The cMUT system as recited in claim 7, wherein the DC bias signal is applied together with the AC carrier signal as a combined modulation signal to the cMUT.

9. The cMUT system as recited in claim 1, wherein, when the cMUT is at a reception operation mode, the output signal has a real signal component and a modulated signal component carrying the real signal component, which contains information of a pressure signal sensed by the cMUT, the cMUT system further comprising:
    a demodulator connected to the reception port for extracting the real signal component from the modulated signal component.

10. The cMUT system as recited in claim 1, wherein, when the cMUT is at a reception operation mode, the output signal has a non-modulated signal component and a modulated signal component carrying a real signal component containing information of a pressure signal sensed by the cMUT, the cMUT system further comprising:
    a band-pass filter connected to the reception port for filtering out the non-modulated signal component.

11. The cMUT system as recited in claim 1, wherein the AC carrier signal has a frequency significantly higher than an operating frequency of the cMUT.

12. The cMUT system as recited in claim 1, wherein the AC carrier signal has an optimal frequency at which the AC carrier signal and a capacitance change of the cMUT generates a modulated signal component at desirably high signal level.

13. The cMUT system as recited in claim 1, further comprising:
    an inductive device connected to the cMUT for tuning impedance of the cMUT.

14. The cMUT system as recited in claim 13, wherein the inductive device is micromachined on a substrate.

15. A capacitive micromachined ultrasonic transducer (cMUT) system comprising:
    a cMUT array having a plurality of cMUTs built on a first substrate, each cMUT having a first electrode and a second electrode;
    at least one of a transmission input signal port and a reception signal port connected to one of the first electrode and the second electrode of each cMUT, wherein the transmission input signal port is adapted for applying a transmission input signal to the connected cMUT in a transmission mode, and the reception signal port is adapted for receiving an output signal from the connected cMUT in a reception mode; and
    an AC signal source for generating an AC carrier signal to be applied to each cMUT through a modulation signal port connected to one of the first electrode and the second electrode of each cMUT; and
    an inductive device array having a plurality of inductive devices built on a second substrate, each inductive device being connected to one of the plurality of cMUTs in the cMUT array, each inductive device having an inductance suitable for tuning impedance of the respective cMUT.

16. The cMUT system as recited in claim 15, wherein the inductive device array is micromachined on the second substrate.

17. The cMUT system as recited in claim 15, wherein the inductive device array and the cMUT array are wire-bonded to electrically connect each inductive device and the respective cMUT.

18. The cMUT system as recited in claim 15, wherein the inductive device array and the cMUT array are directly bonded through contact bonding pads to electrically connect each inductive device and the respective cMUT.

19. A method for transmitting an ultrasonic signal using a cMUT system including a cMUT having a first electrode and a second electrode, at least one of the first electrode and the second electrode being movable and interfacing with a medium, the method comprising:
    applying a transmission input signal having a transmission frequency to one of the first electrode and the second electrode of the cMUT;

applying an AC modulation signal having a carrier frequency to one of the first electrode and the second electrode of the cMUT, wherein the carrier frequency is higher than the transmission frequency; and allowing the movable electrode of the cMUT to move in response to the applied transmission input signal and the AC modulation signal to generate an ultrasonic wave in the medium.

20. The method as recited in claim 19, wherein the transmission frequency is about half of an operating frequency of the cMUT.

21. The method as recited in claim 19, further comprising:

selecting an amplitude of the AC modulation signal such that a desired DC bias pressure is applied on the cMUT.

22. A method for sensing a pressure using a cMUT system including a cMUT having a first electrode and a second electrode, at least one of the first electrode and the second electrode being movable, the method comprising:

allowing a pressure signal to be applied on the movable electrode of the cMUT to generate a capacitance change of the cMUT, the capacity change having a pressure signal frequency frx;

applying an AC modulation signal having a carrier frequency fcarrier;

receiving a first output signal which is contributed by both the capacitance change and the AC modulation signal, wherein the first output signal has a modulated component at the modulated frequency fcarrier−frx or fcarrier+frx; and demodulating the first output signal to generate a second output signal having a component at the pressure signal frequency frx.

23. The method as recited in claim 22, wherein the carrier frequency fcarrier is significantly higher than the pressure signal frequency frx.

24. The method as recited in claim 22, wherein the AC modulation signal has an optimal frequency at which the modulated component at the modulated frequency fcarrier−frx or fcarrier+frx has a desirably high signal level.

25. The method as recited in claim 22, wherein the pressure signal frequency frx is in the range of $Hz \leq fr \leq 20$ kHz.

* * * * *